(12) United States Patent
Sankey et al.

(10) Patent No.: US 9,074,052 B2
(45) Date of Patent: Jul. 7, 2015

(54) COPOLYESTERIMIDES OF POLY(ALKYLENE TEREPHTHALATE)S HAVING HIGH GLASS TRANSITION TEMPERATURE AND FILM MADE THEREFROM

(71) Applicant: DuPont Teijin Films U.S. Limited Partnership, Chester, VA (US)

(72) Inventors: Stephen William Sankey, Redcar (GB); William A. MacDonald, Redcar (GB); David Turner, Redcar (GB); Howard Colquhoun, Reading (GB); Stephen Meehan, Reading (GB)

(73) Assignee: DUPONT TEIJIN FILMS U.S. LIMITED PARTNERSHIP, Chester, VA (US)

( * ) Notice: Subject to any disclaimer, the term of this patent is extended or adjusted under 35 U.S.C. 154(b) by 0 days.

(21) Appl. No.: 14/366,915

(22) PCT Filed: Dec. 18, 2012

(86) PCT No.: PCT/GB2012/053171
§ 371 (c)(1),
(2) Date: Jun. 19, 2014

(87) PCT Pub. No.: WO2013/093446
PCT Pub. Date: Jun. 27, 2013

(65) Prior Publication Data
US 2014/0364582 A1    Dec. 11, 2014

(30) Foreign Application Priority Data

Dec. 21, 2011   (GB) .................................. 1122042.3
Dec. 21, 2011   (GB) .................................. 1122051.4

(51) Int. Cl.
| | | |
|---|---|---|
| C08F 20/00 | (2006.01) | |
| C08G 73/10 | (2006.01) | |
| C08K 5/3412 | (2006.01) | |
| C07D 209/48 | (2006.01) | |
| C08J 5/18 | (2006.01) | |
| C08G 63/685 | (2006.01) | |
| D01F 6/84 | (2006.01) | |

(52) U.S. Cl.
CPC .......... *C08G 73/1082* (2013.01); *C08K 5/3412* (2013.01); *C07D 209/48* (2013.01); *C08J 5/18* (2013.01); *C08G 63/685* (2013.01); *C08G 63/6856* (2013.01); *D01F 6/84* (2013.01)

(58) Field of Classification Search
CPC .................................................... C08K 5/3412
USPC .................................................. 528/310, 347
See application file for complete search history.

(56) References Cited

U.S. PATENT DOCUMENTS

| | | | |
|---|---|---|---|
| 3,917,892 A | 11/1975 | Kawaguchi | |
| 4,902,771 A | 2/1990 | Sugawara | |
| 5,162,455 A * | 11/1992 | Greene .................... | 525/437 |
| 2007/0225410 A1 | 9/2007 | Edwards | |

FOREIGN PATENT DOCUMENTS

| | | |
|---|---|---|
| EP | 0419400 | 2/1996 |
| GB | 1456850 | 11/1976 |
| JP | 11228695 | 8/1999 |
| JP | 2006160940 | 6/2006 |
| WO | 03022575 | 3/2003 |
| WO | 2005073272 | 8/2005 |
| WO | 2006104243 | 2/2006 |
| WO | WO 2009/016388 A1 | 2/2009 |
| WO | WO 2009/127842 A1 | 10/2009 |
| WO | WO 2009/150424 A1 | 12/2009 |
| WO | 2013093446 | 6/2013 |

OTHER PUBLICATIONS

Sato et al (Liquid Crystalline and Fluorescent Properties of Semi-Rigid Poly(ester imide)s Derived from Bismethyl Ester and Bisalcohol Derivatives of 3,3,4,4-Biphenyltetracarboxdiimide, Polymer Journal, vol. 34, No. 3, pp. 158-165 (2002), Mar. 2002.*
USPTO structure search, May 2015.*
Xu Hao et al., "Application status and developoment trend of novel polyester products," China Synthetic Fiber Industry, vol. 31, No. 4, pp. 45-48, Aug. 2008.
Zhang Congrong, "Application of Polyester Film in Foreing Countries," Shanghai Packaging, No. 1, pp. 29, Feb. 2002.
B. Wunderlich, Macromolecular Physics, Academic Press, New York, (1980).
D. Lee et al., "Synthesis and Properties of Thermotropic Liquid Crystalline Polyurethane Elastomers (II): Effect of Structure of Chain Extender Containing Imide Unit," Korea Polymer Journal, 1999, (7), 6, 356-363.

(Continued)

*Primary Examiner* — Gregory Listvoyb
(74) *Attorney, Agent, or Firm* — RatnerPrestia

(57) ABSTRACT

A copolyester comprising repeating units derived from an aliphatic glycol, terephthalic acid, and the monomer of formula (I): wherein n=2, 3 or 4, and films, fibres, moulding compositions and moulded articles made therefrom.

(I)

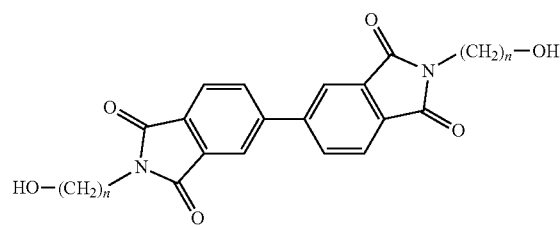

13 Claims, No Drawings

(56) References Cited

OTHER PUBLICATIONS

D. Lee et al., "Synthesis and Properties of Thermotropic Liquid Crystalline Polyurethane Elastomers (III)—Effect of One or Two-step Polymerization Methods," Journal of the Korean Fiber Society, 1999, (36), 12, 873-880, abstract only.
Database Chemcats—Apr. 11, 2011, XP002690776, Accession No. 2042761681.
Database Chemcats—Apr. 11, 2011, XP002690777, Accession No. 0065728262.
Entire patent prosecution history of U.S. Appl. No. 14/366,511, filed Jun. 18, 2014, entitled, "Copolyesterimides of Poly(Alkylene Naphthalates)s Having High Glass Transition Temperature and Film Made Therefrom."
International Preliminary Report for Patentability issued Jun. 24, 2014 for International Application No. PCT/GB2012/053173.
International Preliminary Report on Patentability issued Jun. 24, 2014 for International Application No. PCT/GB2012/053171.
International Search Report for International Application No. PCT/GB2012/053171 mailed Mar. 5, 2013.
International Search Report for International Application No. PCT/GB2012/053173 mailed Feb. 15, 2013.
K. Faghihi "New optical active poly(amide-imide)s derived from N,N'-(4,4-diphthaloyl)-bis-L-leucine and hydantoin derivatives: Synthesis and properties," Chinese chemical letters, 2009, (20), 10, 1153-1156.
Lee Soon Park et al.; "Melt Polymerization of Copoly(ethlene terephthalate-imide)s and Thermal Properties," Journal of applied polymer science, vol. 60, No. 12, p. 2059-2067.
M. Sato, et al., "Preliminary communication Thermotropic semi-rigid copoly(imide-carbonate)s composed of 3,4,3'',4''-p-terphenyltetracarboxdi-imide and 3,4,3',4'-biphenyltetracarboxdi-imide rings," Liquid crystals, 2000, (27), 8, pp. 1123-1128.
M. Sato et al., "Thermotropic liquid-crystalline aromatic-aliphatic polyimides, 6a) Poly(ester-imide)s based on 3, 4:3', 4'-biphenyldicarboximide," Macromolecular Rapid Communications, vol. 15, Mar. 1, 1994, pp. 203-209, ISSN:1022-1336.
M. Sato et al.: "Preparation and thermal properties of semi-rigid homopoly (imide-carbonate)s composed of symmetric aromatic diimide units using diphenyl carbonate," European Polymer Journal, Pergamon press ltd. Oxford. GB, vol. 37, No. 6, Jun. 1, 2001, pp. 1151-1157.
S. Cheng, et al., "Glass Transition and Melting Behavior of Poly(ethylene-2, 6-naphthalenedicarboxylate)," Macromolecules 1988, vol. 21, No. 3, pp. 789-797.
T. Hirata, et al., "Thermotropic liquid-crystalline aromatic-aliphatic polyimides, 3a) Poly (imide-carbonate)s composed of 3, 4:3', 4'-biphenyldicarboximide," Macromol. Chem. Phys., 1994, vol. 195, pp. 1611-1622.

* cited by examiner

COPOLYESTERIMIDES OF POLY(ALKYLENE TEREPHTHALATE)S HAVING HIGH GLASS TRANSITION TEMPERATURE AND FILM MADE THEREFROM

CROSS REFERENCE TO RELATED APPLICATIONS

This application is the National Phase filing of International Application No. PCT/GB2012/053171, filed 18 Dec. 2012, and claims priority of GB Application No. 1122051.4, filed 21 Dec. 2011, and claims priority of GB Application No. 1122042.3, filed 21 Dec. 2011, the entireties of which applications are all incorporated herein by reference for all purposes.

FIELD OF THE INVENTION

The present invention is concerned with novel polyesters and films made therefrom, and methods for their synthesis. In particular, the present invention is concerned with novel copolymers of poly(alkylene terephthalate)s, particularly poly(ethylene terephthalate) (PET), which exhibit improved heat-resistance and thermo-mechanical stability.

BACKGROUND OF THE INVENTION

The glass transition temperature ($T_g$), crystalline melting point ($T_m$) and degree of crystallinity are key parameters in determining the thermo-mechanical properties of polyesters. Previous studies have succeeded in increasing the $T_g$ of thermoplastic polymers, primarily homopolymers, but this has typically been accompanied by a corresponding increase in the $T_m$. Such increases in $T_m$ can be disadvantageous because a thermoplastic polymer should also remain melt-processible (for instance in an extruder), and should preferably remain so under economic conditions (for instance, below about 320° C., preferably below about 300° C., which allows the use of conventional extrusion equipment). At higher processing temperatures, polymer extrusion requires expensive specialist equipment and a great deal of energy, and typically also results in degradation products. The melt-processing temperature should be well below (for instance, at least about 20° C. below) the decomposition temperature of the polymer. In some cases, comonomers have been introduced into polymers in order to increase $T_g$ while retaining $T_m$, but also resulting in convergence of the decomposition temperature and the $T_m$, which leads to the production of degradation products in the melt.

Many attempts have also been made to enhance the glass transition temperature of polyesters by the introduction of more rigid comonomers. However, such comonomers also disrupt the packing of the polymer chains in the crystal lattice, so that while the $T_g$ increases, the $T_m$ and degree of crystallinity typically both decrease as the proportion of comonomer increases, leading ultimately to amorphous materials. In order to fabricate articles from polymeric materials, it is often critical that the polymer exhibit crystallinity to achieve articles with acceptable thermo-mechanical properties.

PET is a semi-crystalline copolymer having a glass transition temperature ($T_g$) of 78° C. and a crystalline melting point of ($T_m$) of 260° C. Many attempts have been made to enhance the $T_g$ of PET by the introduction of more rigid comonomers. Polyether ether ketone (PEEK) is one of the few examples of a high $T_g$ (approximately 143-146° C.) semi-crystalline thermoplastic polymer, and has been used successfully in engineering and biomedical applications. However, PEEK is suitable only for certain types of articles; for instance, it is not suitable for the manufacture of biaxially oriented films. PEEK is also very expensive and has a high crystalline melting point (approximately 350° C.).

SUMMARY OF THE INVENTION

An object of the present invention is to provide polyesters which exhibit improved heat-resistance and thermo-mechanical stability. A further object of the present invention is to provide a thermoplastic polymer with high or increased $T_g$ but without increasing $T_m$ to a point where the polymer is no longer melt-processible under economic conditions (i.e. the polymer should remain melt-processible below about 320° C., preferably below about 300° C.). A further object of the present invention is to provide semi-crystalline polyesters which exhibit high $T_g$ as well as high $T_m$. A further object of the present invention is to increase the $T_g$ of a polyester without significantly decreasing its $T_m$ and/or its degree of crystallinity, and preferably without significantly decreasing its decomposition temperature.

DETAILED DESCRIPTION OF THE INVENTION

As used herein, the term "without significantly decreasing the $T_m$" means that the $T_m$ decreases by no more than 10%, preferably no more than 5%.

As used herein, the term "without significantly decreasing the degree of crystallinity", means that the polyester retains a degree of crystallinity which is commercially useful, preferably in the range of from about 10% to about 60%, preferably from about 20 to about 50%.

A further object of the present invention is to provide a copolyester having a $T_g$ which is higher than the corresponding base polyester, without significantly decreasing its $T_m$ and/or its degree of crystallinity and preferably without significantly decreasing its decomposition temperature.

A further object of the present invention is to provide a comonomer suitable for partial substitution of a monomer in a conventional polyester which increases the $T_g$ of said polyester without significantly decreasing its $T_m$ and/or its degree of crystallinity, and preferably without significantly decreasing its decomposition temperature.

While the objects of the invention do not exclude an increase in $T_m$, any increase in $T_m$ must not be so large that melt-processing becomes uneconomical and that the $T_m$ and decomposition temperature converge.

As used herein, the term "copolyester" refers to a polymer which comprises ester linkages and which is derived from three or more types of comonomers. As used herein, the term "corresponding base polyester" refers to a polymer which comprises ester linkages and which is derived from two types of comonomers comprising ester-forming functionalities, and which serves as a comparator for a copolyester which is derived from comonomers comprising the comonomers of the corresponding base polyester. A comonomer comprising ester-forming functionalities preferably possesses two ester-forming functionalities.

As used herein, the term "semi-crystalline" is intended to mean a degree of crystallinity of at least about 5% measured according to the test described herein, preferably at least about 10%, preferably at least about 15%, and preferably at least about 20%.

Accordingly, the present invention provides a copolyester comprising repeating units derived from an aliphatic glycol, terephthalic acid, and the monomer of formula (I):

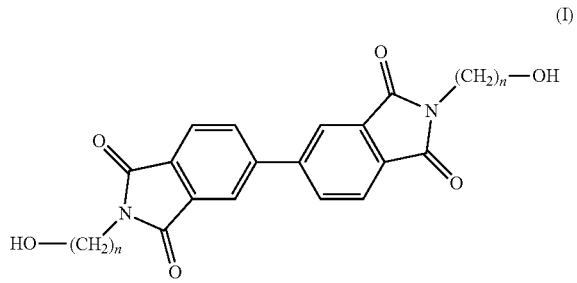

(I)

wherein n=2, 3 or 4, and preferably wherein n=2.

Surprisingly, the present inventors have now found that incorporation of the specific comonomer (I) into a terephthalate polyester not only increases the $T_g$ substantially but does so without significantly decreasing the $T_m$, and without significant detriment to the degree of crystallinity. The copolyesters according to the present invention are thermoplastic. Copolyesters described herein exhibit semi-crystalline properties. The copolyesters according to the present invention can be readily obtained at high molecular weight. The copolyesters according to the present invention can be melt-processed below 320° C. (preferably below 300° C.) into tough, high strength articles. The copolyesters are also referred to herein as co(polyester-imide)s.

The comonomer (I) constitutes a proportion of the glycol fraction of the copolyester. Preferably, the comonomer (I) is present in amounts of no more than about 50 mol % of the glycol fraction of the copolyester, preferably no more than about 40 mol %, preferably no more than about 30 mol %, preferably no more than about 25 mol %, and in one embodiment no more than about 20 mol %, and in a further embodiment no more than about 15 mol %. Preferably, the comonomer (I) is present in amounts of at least about 1 mol % of the glycol fraction of the copolyester. In a preferred embodiment, the comonomer (I) is present in amounts of no more than about 10 mol % of the glycol fraction of the copolyester, preferably no more than about 9 mol %, preferably no more than about 8 mol %, typically no more than about 7 mol %, and in one embodiment no more than about 6 mol %, and preferably at least about 1 mol %. The inventors have observed that even at such relatively low molar fractions of the comonomer (I), small but valuable increases in $T_g$ are observed. For instance, a copolyester based on PET comprising only 5 mol % comonomer (I) where n=2 exhibits a rise of about 13° C. in $T_g$. In an alternative embodiment, the comonomer (I) is present in amounts of greater than 10 mol % of the glycol fraction of the copolyester, and preferably no more than about 50 mol %, preferably no more than about 40 mol %, preferably no more than about 30 mol %, preferably no more than about 25 mol %, and in one embodiment no more than about 20%, and in a further embodiment no more than about 15 mol %.

The aliphatic glycol is preferably selected from $C_2$, $C_3$ or $C_4$ aliphatic diols, more preferably from ethylene glycol, 1,3-propanediol and 1,4-butanediol, more preferably from ethylene glycol and 1,4-butanediol, and is most preferably ethylene glycol. The number of carbon atoms in the aliphatic glycol may be the same or different as the number (n) in the comonomer (I), but it is most preferably the same in order to retain crystallinity, particularly in order to retain crystallinity with increasing amounts of comonomer. Thus, the aliphatic glycol preferably has the formula $HO(CH_2)_mOH$, where m=n.

In one embodiment, the aliphatic glycol is 1,4-butanediol and n=4. In a preferred embodiment, the aliphatic glycol is ethylene glycol and n=2.

The copolyesters can be described by formula (II) below:

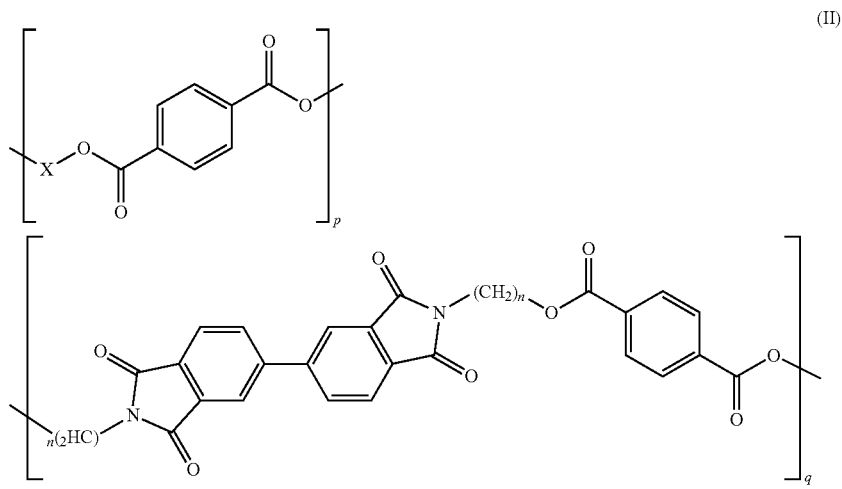

(II)

wherein:

n is as defined for formula (I);

the group X is the carbon chain of said aliphatic glycol;

and p and q are the molar fractions of the aliphatic glycol-containing repeating ester units and the monomer (I)-containing repeating ester units, respectively, i.e. q is no more than 50 (and in a preferred embodiment no more than 10), and p=100−q.

In one embodiment, the copolyester may contain more than one type of aliphatic glycol, and/or more than one type of monomer of formula (I). Preferably, however, the copolyester comprises a single type of aliphatic glycol. Preferably, the copolyester comprises a single type of monomer of formula (I). Preferably, the copolyester comprises a single type of aliphatic glycol, and a single type of monomer of formula (I).

The copolyesters may contain minor amounts of other glycols and in a preferred embodiment such other glycols constitute no more than 10 mol %, preferably no more than 5 mol %, preferably no more than 1 mol % of the total glycol fraction, but in order to maximise performance it is preferred that the glycol fraction consists of comonomer (I) and said aliphatic glycol(s) described above.

The copolyesters of the present invention may contain minor amounts (preferably no more than 10 mol %, preferably no more than 5 mol %, preferably no more than 1 mol % of the total acid fraction) of one or more other dicarboxylic acids (preferably aromatic dicarboxylic acids), for instance including naphthalene-dicarboxylic acid (such as 2,6-naphthalenedicarboxylic acid), isophthalic acid, 4,4'-diphenyldicarboxylic acid, 1,4-cyclohexane dimethanol and 1,6-hexanediol. Where the copolyesters of the present invention contain minor amounts of an aromatic dicarboxylic acid other than terephthalic acid, in one embodiment said aromatic dicarboxylic acid other than terephthalic acid is selected from aromatic dicarboxylic acids other than naphthalene-dicarboxylic acids. Preferably, however, the acid fraction of the copolyesters of the present invention consists of terephthalic acid.

Thus, the copolyester of the present invention preferably contains only aliphatic glycol, terephthalic acid and the monomer of formula (I) defined hereinabove.

The copolyesters of the present invention can be synthesised according to conventional techniques for the manufacture of polyester materials by condensation or ester interchange, typically at temperatures up to about 310° C. Polycondensation may include a solid phase polymerisation stage. The solid phase polymerisation may be carried out in a fluidised bed, e.g. fluidised with nitrogen, or in a vacuum fluidised bed, using a rotary vacuum drier. Suitable solid phase polymerisation techniques are disclosed in, for example, EP-A-0419400 the disclosure of which is incorporated herein by reference. In one embodiment, the aliphatic glycol is reacted with the terephthalic acid to form a bis (hydroxyalkyl)-terephthalate, which is then reacted with the monomer (I) in the desired molar ratios under conditions of elevated temperature and pressure in the presence of a catalyst, as exemplified in Scheme (1) below.

According to a further aspect of the present invention, there is provided the compound of formula (I):

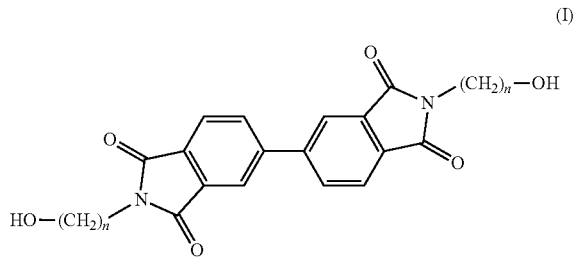

(I)

wherein n=2, 3 or 4, and preferably n=2.

According to a further aspect of the present invention, there is provided a method of synthesis for the compound of formula (I) comprising the step of contacting 4,4'-biphthalic anhydride (also known as 3,3',4,4'-biphenyl tetracarboxylic dianhydride (BPDA)) and an alkanolamine of formula $HO(CH_2)_nNH_2$ (wherein n=2, 3 or 4) in a solvent and heating the mixture (preferably to a temperature in the range of from about 110 to about 140° C., for a period in the range of from about 6 to about 15 hours). Suitable solvents include mixtures of DMAc and toluene. Water by-product is suitably removed from the reaction zone during the course of the reaction, for instance by azeotropic distillation. Further steps in the synthetic and isolation procedure typically comprise:

(i) after the heating step, adding the hot reaction mixture to an approximately equal volume of water, which is then stirred, filtered, washed (for instance with water and then with methanol) and dried;

(ii) boiling the dried solid material in water to remove residual solvent, then filtering hot, washing with methanol, and dried.

The copolyesters of the present invention are suitable for use in applications requiring improved heat-resistance and/or thermo-mechanical performance. The copolyesters of the present invention can be used in fibre form or in moulding compositions.

According to a further aspect of the invention, there is provided a fibre or moulding composition or moulded article comprising a copolyester comprising repeating units derived from an aliphatic glycol, terephthalic acid, and the monomer of formula (I) defined hereinabove. The fibre, moulding composition or moulded article may be produced according to conventional techniques in the art.

The copolyesters of the present invention are also suitable for film manufacture. Biaxially oriented films in particular are useful as base films for magnetic recording media, particularly magnetic recording media required to exhibit reduced track deviation in order to permit narrow but stable track pitch and allow recording of higher density or capacity of information, for instance magnetic recording media suitable as server back-up/data storage, such as the LTO (Linear Tape Open) format. The copolyesters of the present invention are also suitable for the manufacture of film (preferably biaxially oriented film) for use in electronic and opto-electronic devices (particularly wherein the film is required to be flexible) where thermo-mechanically stable backplanes are critical during fabrication of the finished product, for instance in the manufacture of electroluminescent (EL) display devices (particularly organic light emitting display (OLED) devices), electrophoretic displays (e-paper), photovoltaic (PV) cells and semiconductor devices (such as organic field effect transistors, thin film transistors and integrated circuits generally), particularly flexible such devices.

According to a further aspect of the present invention, there is provided a film comprising a copolyester comprising repeating units derived from an aliphatic glycol, terephthalic acid, and the monomer of formula (I) defined hereinabove. The film is preferably an oriented film, preferably a biaxially oriented film. Said copolyester is preferably the major component of the film, and makes up at least 50%, preferably at least 65%, preferably at least 80%, preferably at least 90%, and preferably at least 95% by weight of the total weight of the film. Said copolyester is suitably the only polyester used in the film.

Formation of the film may be effected by conventional extrusion techniques well-known in the art. In general terms the process comprises the steps of extruding a layer of molten polymer at a temperature within an appropriate temperature range, for instance in a range of from about 280 to about 300° C., quenching the extrudate and orienting the quenched extrudate. Orientation may be effected by any process known in the art for producing an oriented film, for example a tubular or flat film process. Biaxial orientation is effected by drawing in two mutually perpendicular directions in the plane of the film to achieve a satisfactory combination of mechanical and physical properties. In a tubular process, simultaneous biaxial orientation may be effected by extruding a thermoplastics polyester tube which is subsequently quenched, reheated and then expanded by internal gas pressure to induce transverse orientation, and withdrawn at a rate which will induce longitudinal orientation. In the preferred flat film process, the film-forming polyester is extruded through a slot die and rapidly quenched upon a chilled casting drum to ensure that the polyester is quenched to the amorphous state. Orientation is then effected by stretching the quenched extrudate in at least one direction at a temperature above the glass transition temperature of the polyester. Sequential orientation may be effected by stretching a flat, quenched extrudate firstly in one direction, usually the longitudinal direction, i.e. the forward direction through the film stretching machine, and then in the transverse direction. Forward stretching of the extrudate is conveniently effected over a set of rotating rolls or between two pairs of nip rolls, transverse stretching then being effected in a stenter apparatus. Stretching is generally effected so that the dimension of the oriented film is from 2 to 5, more preferably 2.5 to 4.5 times its original dimension in the or each direction of stretching. Typically, stretching is effected at temperatures higher than the $T_g$ of the polyester, preferably about 15° C. higher than the $T_g$. Greater draw ratios (for example, up to about 8 times) may be used if orientation in only one direction is required. It is not necessary to stretch equally in the machine and transverse directions although this is preferred if balanced properties are desired.

A stretched film may be, and preferably is, dimensionally stabilised by heat-setting under dimensional support at a temperature above the glass transition temperature of the polyester but below the melting temperature thereof, to induce the desired crystallisation of the polyester. During the heat-setting, a small amount of dimensional relaxation may be performed in the transverse direction (TD) by a procedure known as "toe-in". Toe-in can involve dimensional shrinkage of the order 2 to 4% but an analogous dimensional relaxation in the process or machine direction (MD) is difficult to achieve since low line tensions are required and film control and winding becomes problematic. The actual heat-set temperature and time will vary depending on the composition of the film and its desired final thermal shrinkage but should not be selected so as to substantially degrade the toughness properties of the film such as tear resistance. Within these constraints, a heat set temperature of about 180 to 245° C. is generally desirable. After heat-setting the film is typically quenched rapidly in order induce the desired crystallinity of the polyester.

In one embodiment, the film may be further stabilized through use of an in-line relaxation stage. Alternatively the relaxation treatment can be performed off-line. In this additional step, the film is heated at a temperature lower than that of the heat-setting stage, and with a much reduced MD and TD tension. The tension experienced by the film is a low tension and typically less than 5 kg/m, preferably less than 3.5 kg/m, more preferably in the range of from 1 to about 2.5 kg/m, and typically in the range of 1.5 to 2 kg/m of film width. For a relaxation process which controls the film speed, the reduction in film speed (and therefore the strain relaxation) is typically in the range 0 to 2.5%, preferably 0.5 to 2.0%. There is no increase in the transverse dimension of the film during the heat-stabilisation step. The temperature to be used for the heat stabilisation step can vary depending on the desired combination of properties from the final film, with a higher temperature giving better, i.e. lower, residual shrinkage properties. A temperature of 135 to 250° C. is generally desirable, preferably 150 to 230° C., more preferably 170 to 200° C. The duration of heating will depend on the temperature used but is typically in the range of 10 to 40 seconds, with a duration of 20 to 30 seconds being preferred. This heat stabilisation process can be carried out by a variety of methods, including flat and vertical configurations and either "off-line" as a separate process step or "in-line" as a continuation of the film manufacturing process. Film thus processed will exhibit a smaller thermal shrinkage than that produced in the absence of such post heat-setting relaxation.

The film may further comprise any other additive conventionally employed in the manufacture of polyester films. Thus, agents such as anti-oxidants, UV-absorbers, hydrolysis stabilisers, cross-linking agents, dyes, fillers, pigments, voiding agents, lubricants, radical scavengers, thermal stabilisers, flame retardants and inhibitors, anti-blocking agents, surface active agents, slip aids, gloss improvers, prodegradents, viscosity modifiers and dispersion stabilisers may be incorporated as appropriate. Such components may be introduced into the polymer in a conventional manner. For example, by mixing with the monomeric reactants from which the film-forming polymer is derived, or the components may be mixed with the polymer by tumble or dry blending or by compounding in an extruder, followed by cooling and, usually, comminution into granules or chips. Masterbatching technology may also be employed. The film may, in particular, comprise a particulate filler which can improve handling and windability during manufacture, and can be used to modulate optical properties. The particulate filler may, for example, be a particulate inorganic filler (e.g. metal or metalloid oxides, such as alumina, titania, talc and silica (especially precipitated or diatomaceous silica and silica gels), calcined china clay and alkaline metal salts, such as the carbonates and sulphates of calcium and barium).

The thickness of the film can be in the range of from about 1 to about 500 typically no more than about 250 and typically no more than about 150 Particularly where the film of the present invention is for use in magnetic recording media, the thickness of the multilayer film is suitably in the range of from about 1 to about 10 more preferably from about 2 to about 10 µm, more preferably from about 2 to about 7 µm, more preferably from about 3 to about 7 µm and in one embodiment from about 4 to about 6 µm. Where the film is to be used as a layer in electronic and display devices as described herein, the thickness of the multilayer film is typically in the range of from about 5 to about 350 µm preferably no more than about 250 µm, and in one embodiment no more than about 100 µm, and in a further embodiment no more than about 50 µm, and typically at least 12 µm, more typically at least about 20 µm.

According to a further aspect of the invention, there is provided an electronic or opto-electronic device comprising the film (particularly the biaxially oriented film) described herein, particularly electronic or opto-electronic devices such as electroluminescent (EL) display devices (particularly organic light emitting display (OLED) devices), electrophoretic displays (e-paper), photovoltaic (PV) cells and semiconductor devices (such as organic field effect transistors, thin film transistors and integrated circuits generally), particularly flexible such devices.

According to a further aspect of the invention, there is provided a magnetic recording medium comprising the film (particularly the biaxially oriented film) described herein as a base film and further comprising a magnetic layer on one surface thereof. The magnetic recording medium includes, for example, linear track system data storage tapes such as QIC or DLT, and, SDLT or LTO of a further higher capacity type. The dimensional change of the base film due to the temperature/humidity change is small, and so a magnetic recording medium suitable to high density and high capacity causing less track deviation can be provided even when the track pitch is narrowed in order to ensure the high capacity of the tape.

The following test methods were used to characterise the properties of the novel compounds disclosed herein.

(i) Glass transition temperature ($T_g$); temperature of cold crystallisation ($T_{cc}$), crystalline melting point ($T_m$) and degree of crystallinity ($X_c$) were measured by differential scanning calorimetry (DSC) using a Universal V4.5A machine (TA Instruments) according to the following test method and otherwise according to the method described in ASTM E1356-98. The sample was maintained under an atmosphere of dry nitrogen for the duration of the scan (approx. 1.5 to 3 hours). The sample (4-6 mg) was heated from 20° C. to 300° C. at a rate of 20° C./min, held at 300° C. for 5 minutes, and then cooled to 20° C. at a rate of 20° C./min, and then heated from 20° C. to 350° C. at 10° C./min. The thermal properties were recorded on the second heating scan.

The value of $T_g$ was taken as the extrapolated onset temperature of the glass transition observed on the DSC scan (heat flow (W/g) against temperature (° C.)), as described in ASTM E1356-98.

The values of $T_{cc}$ and $T_m$ were taken from the DSC scan as the temperature at which peak heat flow was observed in the respective transitions.

The degree of crystallinity $(X_c)$ was calculated according to the equation:

$$X_c \Delta H_m / \Delta H_m°$$

wherein:
$\Delta H_m$ = experimental enthalpy of fusion calculated from the integral of the melting endotherm;
$\Delta H_m°$ = theoretical enthalpy of fusion of the corresponding poly(alkylene-terephthalate) homopolymer (i.e. without the co-monomer of formula (I)) at 100% crystallinity. Thus, for copolyesters of the present invention comprising repeating units derived from ethylene glycol, terephthalic acid and the co-monomer of formula (I), $\Delta H_m°$ is the theoretical enthalpy of fusion of a 100% crystalline PET polymer (140 J/g) as defined in the literature (B. Wunderlich, *Macromolecular Physics*, Academic Press, New York, (1976)).

Herein, the degree of crystallinity is measured for samples which have been annealed at 200° C. for 2 hours. The annealing of the sample was conducted during a DSC heating cycle. The full heating cycle for these crystallinity measurements was as follows:
(i) Heated from 20 to 300° C. at 20° C./min
(ii) Held at 300° C. for 5 minutes
(iii) Cooled to 20° C. at 20° C./min
(iv) Heated to 200° C. at 20° C./min
(v) Held at 200° C. for 120 min
(vi) Cooled to 20° C.
(vii) Heated from 20 to 400° C. at 10° C./min.

The thermal properties were recorded on the final heating scan.

(ii) Inherent viscosity $(\eta_{inh})$ was determined at 25° C. for 0.1% w/v solutions of the polymer in $CHCl_3$/TFA (2:1) using a Schott-Geräte CT-52 auto-viscometer, with capillary No. 53103. Inherent viscosities were calculated as:

$$\eta_{inh} = ln[(t_2/t_1)/c]$$

wherein:
$\eta_{inh}$ = Inherent Viscosity (dL/g)
$t_1$ = Flow time of solvent (s)
$t_2$ = Flow time of the polymer solution (s)
c = Concentration of the polymer (g/dL)

The invention is further illustrated by the following examples. It will be appreciated that the examples are for illustrative purposes only and are not intended to limit the invention as described above. Modification of detail may be made without departing from the scope of the invention.

EXAMPLES

A reaction scheme to prepare copolyesters of the present invention is in Scheme 1.

Scheme 1. Synthesis of comonomer 1 and its copolymerisation with bis(hydroxyethyl terephthalate) to give a family of co(polyester0imide)s (2) (where z in Scheme 1 is the degree of polymerisation of the overall copolymer).

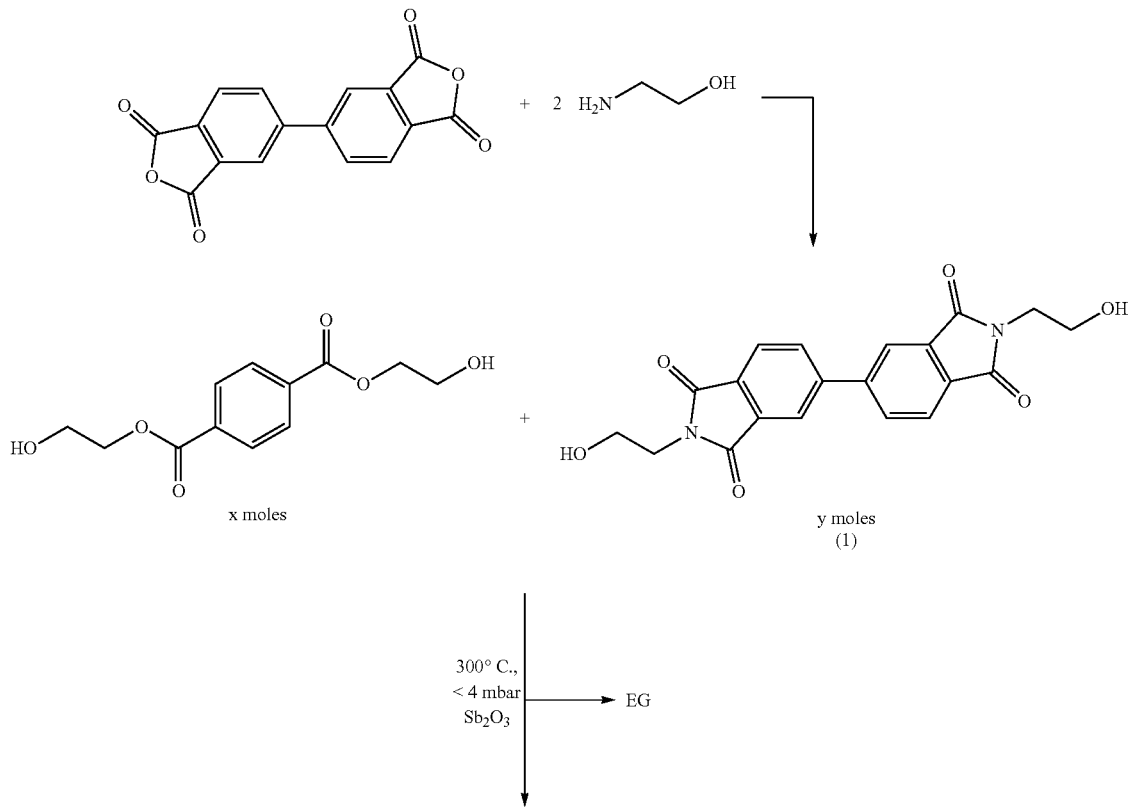

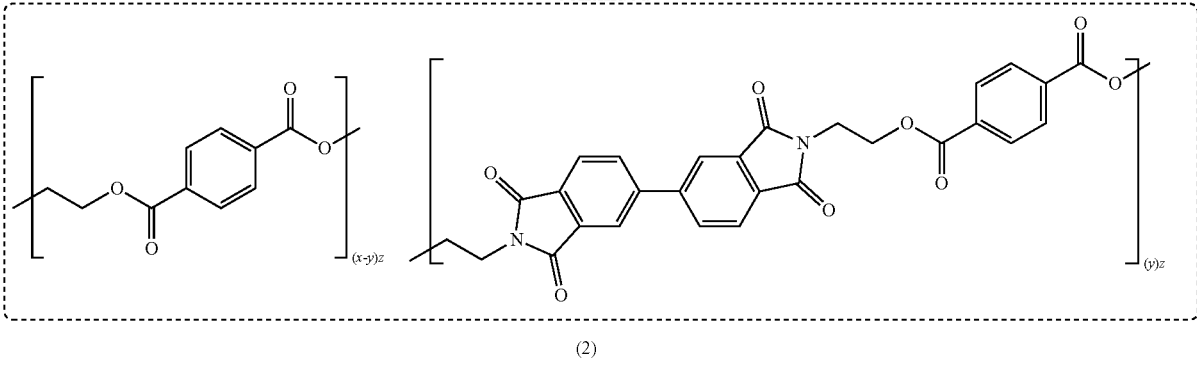

(2)

Example 1

Synthesis of N,N'-bis-(2-hydroxyethyl)-4,4'-biphthalimide (Monomer 1)

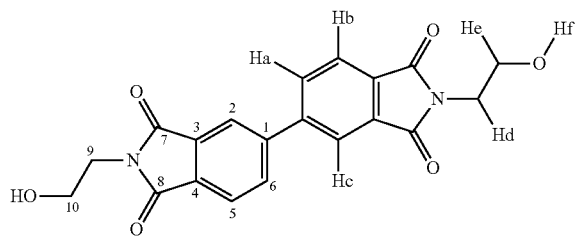

4,4'-biphthalic dianhydride (5.65 g, 19.20 mmol), ethanolamine (2.4 ml, 39.37 mmol), DMAc (40 ml) and toluene (35 ml) were charged to a 250 ml round bottom flask and heated to 130° C. overnight. Dean-Stark apparatus was used to azeotropically distill off the water by-product. The hot reaction mixture was then added to water (~400 ml) upon which a white precipitate formed. This was then stirred for 6 hours, filtered, washed with water (2×40 ml) and MeOH (2×40 ml) and dried in a vacuum oven at 100° C. overnight. Residual solvent was removed as the product was boiled in water (40 ml) for 4 hours then filtered hot, washed with MeOH (2×25 ml), filtered and dried in a vacuum oven at 80° C. overnight. The isolated product was a white powder. (6.21 g, 81%), m.p. (DSC) 286° C., $^1$HNMR (400 MHz, DMSO) δ(ppm) 8.22 (m, 4H$_{b+c}$), 7.97 (d, J=8.16 Hz, 2H$_a$), 4.85 (t, J=11.96 Hz, 2H$_f$), 3.67 (t, J=11.28 Hz, 4H$_d$), 3.59 (m, 4H$_e$), $^{13}$C NMR (400 MHz, DMSO) 167.48 (C$_{7+8}$), 144.00 (C$_1$), 137.17 (C$_6$), 132.75 (C$_4$), 131.42(C$_3$), 123.53 (C$_5$), 121.68 (C$_2$), 57.90 (C$_9$), 40.42 (C$_{10}$), IR: 3445, 2944, 1763, 1684, 1384, 1011, 739 cm$^{-1}$.

Example 2

Synthesis of a Copolymer of PET Containing 5 mol % of Monomer 1

Bis-(2-hydroxyethyl)terephthalate (4.7513 g, 18.70 mmol), N,N'-bis-(2-hydroxyethyl)-4,4'-biphthalimide (0.3743 g, 0.98 mmol) and Sb$_2$O$_3$ (1.5 mg, 5.1×10$^{-3}$ mmol) were charged to a Schlenk tube fitted with a rubber sealed stirrer guide and a glass stirrer rod. The reaction mixture was heated to 200° C. over 30 minutes by use of a tube furnace under an inert nitrogen atmosphere and held at that temperature for 10 minutes. A stirring rate of 300 rpm was applied via a mechanical stirrer and the reaction mixture was heated to 290° C. over 45 min. A vacuum of 0.5 torr was applied and the temperature was maintained for 30 min where the melt became increasingly more viscous. After this time nitrogen was purged through the system, the stirrer was removed and the mixture was allowed to cool. The reaction tube was cut and the glass tubing containing the polymer was broken up. The polymer was dissolved away from the glass and the stirrer in a solution of CHCl$_3$/TFA (2:1) (~50 ml) and the glass was filtered off. The pale yellow solution was concentrated in vacuo to ~10-15 ml and added dropwise into MeOH (~120 ml). The white polymer beads were filtered, washed with MeOH (2×15 ml) and Dried in a vacuum oven overnight. T$_g$=87°C., T$_{cc}$=163°C., T$_m$=242°C., ΔH$_m$=31 Jg$^{-1}$, η$_{inh}$=0.53 dLg$^{-1}$. The product was fully soluble in chloroform/trifluoroacetic acid and in hexafluoropropan-2-ol.

The experimental data for the Examples are summarised in Table 1 below.

TABLE 1

| Sample | Polymer | T$_g$ (° C.) | T$_{cc}$ (° C.) | T$_m$ (° C.) | ΔH$_m$ (J/g) | Xc (%) | Viscosity (gdL$^{-1}$) |
|---|---|---|---|---|---|---|---|
| Control | PET | 75 | — | 257 | 44 | 31 | 0.80 |
| Ex. 2 | PETcoBPDI-5 | 87 | 163 | 242 | 31 | 22 | 0.53 |

The control sample is pure PET, synthesised in accordance with the procedure described for Example 2 but without the inclusion of N,N'-bis-(2-hydroxyethyl)-4,4'-biphthalimide, and with a 1-hour reaction time.

The polymer of Example 2 was then melt-pressed to form a thin, tough film (approx. 0.5 mm thick; approx. 2-3mm wide and approx. 2 cm long) which could be oriented by hot-drawing to at least six times its original extension.

The invention claimed is:

1. A copolyester comprising repeating units derived from an aliphatic glycol, terephthalic acid, and the monomer of formula (I):

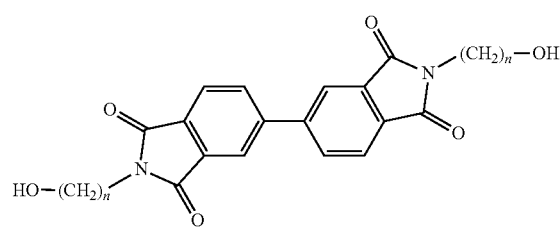

(I)

wherein n=2, 3 or 4, and wherein comonomer (I) constitutes a proportion of the glycol fraction of the copolyester.

2. The copolyester according to claim 1 which has formula (II):

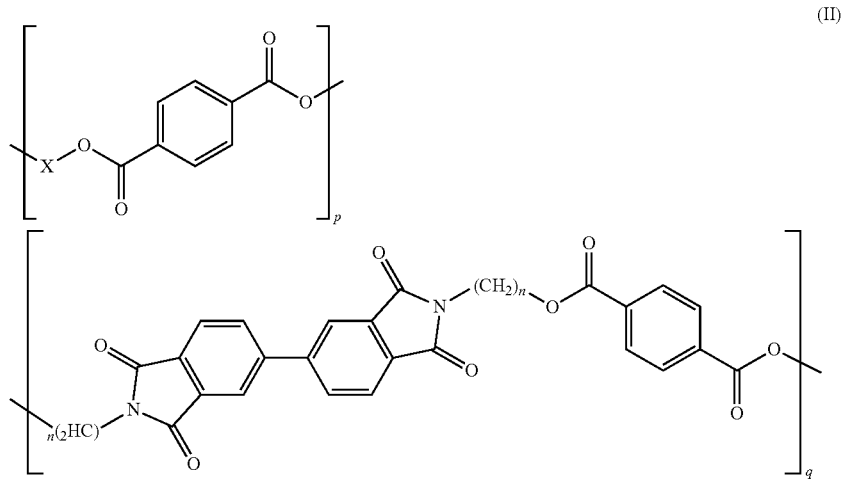

wherein:
n=2, 3 or 4;
the group X is the carbon chain of said aliphatic glycol; and
p and q are the molar fractions of the aliphatic glycol-containing repeating ester units and the monomer (I)-containing repeating ester units, respectively.

3. The copolyester according to claim 1, wherein the monomer (I) is present at a level of no more than about 50 mol % of the glycol fraction of the copolyester.

4. The copolyester according to claim 1, wherein the monomer (I) is present at a level of no more than about 10 mol % of the glycol fraction of the copolyester.

5. The copolyester according to claim 1, wherein the monomer (I) is present at a level of at least about 1 mol % of the glycol fraction of the copolyester.

6. The copolyester according to claim 1, wherein the aliphatic glycol is selected from $C_2$, $C_3$ and $C_4$ aliphatic diols.

7. The copolyester according to claim 1, wherein the aliphatic glycol is ethylene glycol.

8. The copolyester according to claim 1, wherein the number of carbon atoms in the aliphatic glycol is the same as the number (n) in comonomer (I).

9. The copolyester according to claim 1, wherein n=2.

10. A polyester film comprising a copolyester according to claim 1.

11. A fibre or moulding composition or moulded article comprising a copolyester according to claim 1.

12. The polyester film according to claim 10, wherein the film is oriented.

13. The polyester film according to claim 10, wherein the film is biaxially oriented.

* * * * *